United States Patent [19]
Barr et al.

[11] Patent Number: 6,051,216
[45] Date of Patent: Apr. 18, 2000

[54] COSMETIC COMPOSITION CONTAINING SILOXANE BASED POLYAMIDES AS THICKENING AGENTS

[75] Inventors: Morton L. Barr, East Brunswick, N.J.; Heng Cai, Yardley, Pa.; Anthony Esposito, Roselle; Joel Freundlich, Monmouth Junction, both of N.J.; Douglas W. King, Midland, Mich.; Michael Mendolia, Bridgewater; Bhalchandra Moghe, White House Station, both of N.J.; Lenin James Petroff, Bay City, Mich.; Thomas Schamper, Cranbury, N.J.; Michael Ward Skinner, Midland, Mich.; Paul Joseph Vincenti, Jefferson; Ching-min Kimmy Wu, Kendall Park, both of N.J.; Kenneth Edward Zimmerman, Mt. Pleasant, Mich.; Dennis J. Colwell, East Windsor, N.J.

[73] Assignees: Colgate-Palmolive Company, New York, N.Y.; Dow Corning Corporation, Midland, Mich.

[21] Appl. No.: 08/904,709

[22] Filed: Aug. 1, 1997

[51] Int. Cl.$^7$ ................................................ A61K 7/32
[52] U.S. Cl. .................... 424/78.35; 424/65; 424/401; 424/DIG. 5; 514/944
[58] Field of Search .................... 424/401, 65, 78.35, 424/DIG. 5; 514/944

[56] References Cited

U.S. PATENT DOCUMENTS

| | | |
|---|---|---|
| 4,322,400 | 3/1982 | Yuhas . |
| 4,604,442 | 8/1986 | Rich . |
| 4,673,570 | 6/1987 | Soldati . |
| 4,853,214 | 8/1989 | Orr . |
| 4,937,069 | 6/1990 | Shin . |
| 5,019,375 | 5/1991 | Tanner et al. . |
| 5,069,897 | 12/1991 | Orr . |
| 5,102,656 | 4/1992 | Kasat . |
| 5,120,531 | 6/1992 | Wells et al. . |
| 5,243,010 | 9/1993 | Choi et al. . |
| 5,272,241 | 12/1993 | Lucarelli et al. . |
| 5,500,209 | 3/1996 | Ross et al. . |
| 5,603,925 | 2/1997 | Ross et al. . |
| 5,874,069 | 2/1999 | Mendolia et al. . |
| 5,919,441 | 7/1999 | Mendolia et al. ................ 424/78.08 |

FOREIGN PATENT DOCUMENTS

| | | |
|---|---|---|
| 291334 A2 | 11/1988 | European Pat. Off. . |
| 0545002 | 6/1993 | European Pat. Off. . |
| 2147305 | 5/1985 | United Kingdom . |
| WO 92/05767 | 4/1992 | WIPO . |
| WO 9736572 | 10/1997 | WIPO . |
| WO9736573 | 10/1997 | WIPO . |

OTHER PUBLICATIONS

Patent Abstract of Japan: Kao Corportation, JP07 173395A, Nov. 30, 1995, vol. 95, No. 010.

*Primary Examiner*—Jyothsna Venkat
*Attorney, Agent, or Firm*—Rosemary Miano; James DeCasare

[57] ABSTRACT

An invention is disclosed which comprises siloxane-based polyamides as gelling agents for cosmetic products, methods for making such agents, formulations therof and cosmetic formulations therewith. These polyamides contain siloxane groups in the main chain and act to thicken compositions containing volatile and/or non-volatile silicone fluids. Cosmetic compositions may be made by adding at least one active ingredient such as an antiperspirant.

20 Claims, No Drawings

COSMETIC COMPOSITION CONTAINING SILOXANE BASED POLYAMIDES AS THICKENING AGENTS

BACKGROUND OF THE INVENTION

The present invention is directed to novel polyamide gelling agents, methods of making such agents and cosmetic agents made therefrom.

While a number of references have disclosed polyamides as a class of compounds, it has been found that certain groups of polyamides containing siloxane portions are novel and are useful in making excellent cosmetic products, especially antiperspirants and deodorants.

Cosmetic compositions (for example, a solid cosmetic composition, such as a gel, soft-solid or semi-solid (cream), or stick), are comprised of a base composition containing at least one silicone fluid (for example, silicone liquids such as silicone oils) which is thickened using a siloxane-based polyamide as a gelling agent; a carrier in which cosmetically active materials are incorporated; and at least one active ingredient to provide the activity for such cosmetic composition. Particular embodiments of the present invention include deodorant and antiperspirant compositions (and base compositions therefor), in which the cosmetically active ingredient is a deodorant active material and/or an antiperspirant active material. Embodiments of the present invention are not limited, however, to such antiperspirant and/or deodorant compositions, and are also directed to other cosmetic compositions containing other cosmetically active ingredients, such as sun protection compositions containing sunscreen agents as the active material.

Preferred embodiments of formulated cosmetic products are directed to cosmetic compositions which are transparent (clear), including solid transparent (clear) compositions, especially transparent (clear) deodorant and/or antiperspirant compositions which are sticks or gels. While selected embodiments of cosmetic compositions made with the polyamides described are preferably clear or transparent, the cosmetic compositions need not, however, be clear or transparent, and can be translucent, or opaque.

The compounds described herein and used as gelling agents in this invention are selected siloxane-based polyamides and mixtures thereof. Preferably compositions made with the siloxane-based polyamides have improved application and cosmetic properties (including reduced tackiness and stickiness), and, more preferably, have improved clarity/low residue properties.

Antiperspirant products are well known in the art. Antiperspirant products have appeared in the marketplace in various dosage forms, such as sticks, gels, roll-ons, aerosols and creams. Generally, these dosage forms include a solution of the active ingredient in a solvent, a suspension of the active ingredient in a non-solvent, or a multi-phase dispersion or emulsion in which a solution of the active ingredient is dispersed in some continuous phase or in which the solubilized active ingredient constitutes a continuous phase.

Of the above-referred-to dosage forms, the roll-on is an example of a liquid form composition, the stick form is an example of a solid form composition, and the gel form is a thickened form which may or may not be a solid (for example, under some circumstances gels can flow). The stick form can be distinguished from a gel on the basis that in a stick the formulated product can maintain its shape for extended time periods outside the package (allowing for some shrinkage due to solvent evaporation), while a gel cannot so maintain its shape. Adjustment of amounts of gelling or thickening agents such as bentones, fumed silica, polyethylene, stearyl alcohol or castor wax, can be used in order to form a gel or stick.

Gels, pastes and creams (which are also known as soft-solids or semi-solids) can be suitably packaged in containers which have the appearance of a stick, but which dispense through apertures (for example, slots or pores) on the top surface of the package. These products have been called soft sticks or "smooth-ons". These products hereinafter are generically called "gels". Reference is made to U.S. Pat. No. 5,102,656 to Kasat, No. 5,069,897 to Orr, and No. 4,937,069 to Shin, each of which discloses such gels, including physical characteristics thereof such as viscosity and hardness. The contents of each of these three U.S. patents are incorporated herein by reference in their entirety.

A representative composition which can be dispensed through apertures is described in U.S. Pat. No. 5,102,656 to Kasat. This disclosed composition is a creamy, heterogeneous anhydrous antiperspirant product containing, in percent by weight, of the total weight of the composition, 30%–70% of a volatile silicone as a carrier, 7–30% of a suitable gelling agent or agents, and about 12–30% of a physiologically acceptable antiperspirant agent. This patent discloses that the gelling agent can be any of a number of materials, including, for example, hydrogenated vegetable oil, hydrogenated castor oil, fatty acids having from 14 to 36 carbon atoms, beeswax, paraffin wax, fatty alcohols having from 14 to 24 carbon atoms, polyethylene and the like.

Recently, there has been significant activity in developing clear or translucent antiperspirant sticks and gels. Clear or translucent sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional active antiperspirant materials are acidic, much work has been involved in discovering suitable stabilizing or buffering agents to prevent or slow down acid attack on the acetal gelling agent. Such work has not been completely successful. Moreover, these clear or translucent antiperspirant sticks containing the acetal gelling agent and including a solubilized active antiperspirant material, have the disadvantage of being inherently tacky. Thus, development work in connection with these clear or translucent antiperspirant sticks containing the acetal gelling agent has also focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Clear or translucent antiperspirant gels (which have been dispensed from containers having the appearance of a stick) have been marketed, consisting of viscous, high internal phase emulsions. These gels exhibit some advantages over the aforementioned acetal-based clear sticks, in that the selection of formulation ingredients is less restricted (for example, water can be used), and often tack can be reduced significantly. But these emulsions suffer from various disadvantages, including often requiring the use of ethanol to achieve desired aesthetics. In connection with these emulsions, see U.S. Pat. No. 4,673,570 to Soldati and PCT (International Application) Publication No. WO 92/05767.

U.S. Pat. No. 5,120,531 to Wells, et al discloses rinse-off hair conditioner and styling compositions providing a gelnetwork thickened vehicle for the styling polymer and solvent. This patent discloses various siloxanes as the conditioning agent including polydiorganosiloxanes having quaternary ammonium-substituted groups attached to the silicon, and polydiorganosiloxanes having silicone-bonded substituents which are amino-substituted hydrocarbon groups.

U.S. Pat. No. 5,500,209, the contents of which are incorporated herein by reference in their entirety, discloses a gel or stick which includes active deodorant and/or antiperspirant ingredients, a polyamide gelling agent, and a solvent for the polyamide gelling agent, which gel or stick composition can be clear or translucent. This patent discloses that the polyamide gelling agent is soluble in a cosmetically acceptable solvent at elevated temperatures, and solidifies (gels) upon cooling; acceptable solvents are disclosed as including various alcohols, including various glycols. While the polyamide-containing stick or gel disclosed in the aforementioned patent contains desirable properties in connection with stability of the composition, (particularly in the presence of acidic antiperspirant active materials, and in providing clear or translucent gel or stick compositions) such formulas may result in tackiness and stickiness both upon and after application to the skin.

Addressing this problem of tackiness and stickiness in connection with cosmetic compositions utilizing a polyamide gelling agent, U.S. Pat. No. 5,603,295, the contents of which are incorporated herein by reference in their entirety, discloses use of a specific solvent system for a solid composition containing an antiperspirant active material and a polyamide gelling agent. This solvent system is glycol-free and contains a non-ionic surfactant and a polar solvent. Water is the polar solvent, and with the non-ionic surfactant acts as a dispersing medium for the antiperspirant active material, in which sufficient water is used to give a clear or translucent solution/emulsion of the antiperspirant active material.

A typical technique to reduce the tackiness of, for example, antiperspirant formulations is the incorporation of cyclomethicone (tetra- penta- or hexacyclodimethyl-siloxanes or mixtures thereof). This cyclomethicone is a very low-viscosity liquid that provides excellent lubricity and does not leave stains on the skin and/or clothing. More than 50% by weight of cyclomethicone has been incorporated into solid stick antiperspirant formulations, for example, using a wax solidifying agent. However, cyclomethicone is a nonsolvent for the dimer based polyamides described as gelling agents in U.S. Pat. No. 5,500,209. Moreover, only limited quantities of the cyclomethicone can be incorporated in solid compositions gelled using such polyamide gelling agent, without destroying the clarity of the gelled composition. Beyond that point, the gelled composition becomes cloudy because of either excessive crystallization of the polyamide or immiscibility of the cyclomethicone in the mixture.

U.S. Pat. No. 5,243,010 to Choi, et al., discloses aromatic polyamide resins having pendant silyl groups.

U.S. Pat. No. 5,272,241 to Lucarelli, et al., discloses organofunctional siloxanes useful in both the personal care and plastics industries, the siloxanes being amino acid functionalized silicones.

U.S. patent application Ser. No. 08/790,351 filed Jan. 24, 1997, now published as WO97/36572 assigned to The Mennen Company describes in general the use of polyamides as gelling agents for cosmetic compositions.

Notwithstanding the foregoing, there is still a need for improved siloxane-based polyamide gelling agents and cosmetic compositions made therefrom, especially when the base compositions made with the polyamides are capable of forming cosmetic products having improved clarity. Moreover, it is also desired to provide such base compositions, thickened utilizing such gelling agent, which are transparent and clear, and can be formed into products having varying degrees of firmness, such as from a cream to a stick, depending on amounts of thickening agent contained in the composition.

Thus, it is an object of the present invention to provide a base composition, in which a cosmetically active material can be incorporated to form a cosmetic composition for example, an antiperspirant and/or deodorant, wherein the base composition is thickened using a selected siloxane-based polyamide gelling agent.

It is a further object of the present invention to provide a base composition which is capable of exhibiting improved aesthetics such as clarity and which preferably leaves no visible (white) residue upon application and after drying.

It is an overall object of the present invention to provide siloxane-based polyamides polymers which can be used as gelling agents to thicken cosmetic compositions, which polymers are compatible with volatile and/or non-volatile silicone liquids.

Objects of the present invention also include providing a cosmetic composition including this base composition and cosmetically active materials and methods of using this cosmetic composition.

SUMMARY OF THE INVENTION

The foregoing objects are achieved by the present invention which comprises forming novel siloxane-based polyamides and using the polyamides as gelling agents to formulate cosmetic compositions such as deodorants and antiperspirants. The selected polyamides described herein exhibit superior performance when used to form cosmetic compositions. The polyamides of this invention are multiples of a unit represented by the following Formula A:

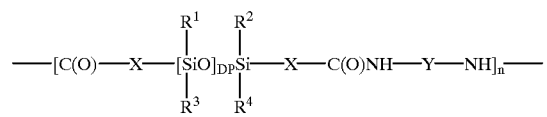

Formula A where:
(1) DP is selected from the group consisting of 1–700, preferably 15–500, and more preferably 15–45. DP represents an average value for degree of polymerization of the siloxane units in the polymer with greater or lesser DP values centered around the indicated DP value.
(2) n is a number selected from the group consisting of 1–500, particularly 1–100, more particularly 4–25.
(3) X is a linear or branched chain alkylene having 1–30 carbons, particularly 3–10 carbons and, more particularly, 10 carbons.
(4) Y is selected from the group consisting of linear or branched chain alkylenes having 1–40 carbons, particularly 1–20 carbons, more particularly 2–6 carbons and, especially 6 carbons, wherein
   (a) The alkylene group may optionally and additionally contain in the alkylene portion at least one of (i) 1–3 amide linkages; (ii) C5 or C6 cycloalkane; and (iii)

phenylene optionally substituted by 1–3 members selected independently from the group consisting of C1–C3 alkyls; and (b) the alkylene group itself may optionally be substituted by at least one member selected from the group consisting of (i) hydroxy; (ii) C3–C8 cycloalkane; (iii) 1–3 members selected independently from the group consisting of C1–C3 alkyls; phenyl optionally substituted by 1–3 members selected independently from the group consisting of C1–C3 alkyls; (iv) C1–C3 alkyl hydroxy; and (v) C1–C6 alkyl amine; or Y=Z where Z=T($R^{20}$)($R^{21}$)($R^{22}$) where each of $R^{20}$, $R^{21}$ and $R^{22}$ are independently selected from the group consisting of linear and branched C1–C10 alkylenes; and T is selected from the group consisting of CR, where R is selected from hydrogen, the group consisting of the group defined for $R^1$–$R^4$, and a trivalent atom selected from N, P and Al.

(5) Each of $R^1$–$R^4$ (collectively "R") is independently selected from the group consisting of methyl, ethyl, propyl, isopropyl, a siloxane chain, and phenyl, wherein the phenyl may optionally be substituted by 1–3 members from the group consisting of methyl and ethyl. More particularly, values for $R^1$–$R^4$ are selected from methyl and ethyl and especially methyl. The values for X, Y, DP, and $R^1$–$R^4$ may be the same or different for each unit of the polyamide.

By siloxane groups we mean groups having siloxane units:

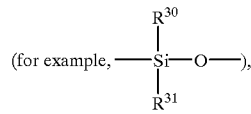

(for example,)

where $R^{30}$ and $R^{31}$ are each independently selected from the group consisting of organic moieties, and each of $R^{30}$ and $R^{31}$ are connected to the silicon by a carbon-silicon bond.

The carbon numbers in the alkylene chain do not include the carbons in the extra segments or substitutions. Also, the polyamides must have a siloxane portion in the backbone and optionally may have a siloxane portion in a pendant or branched portion.

If repeated with no variations in the defined variables, Formula A is representative of a linear homopolymer. Acceptable variations of the invention include: (1) polyamides in which multiple values of DP, X, Y, and $R^1$–$R^4$ occur in one polymeric molecule, wherein the sequencing of these units may be alternating, random or block; (2) polyamides in which an organic triamine or higher amine such as tris(2-aminoethyl)amine replaces the organic diamine in part, to produce a branched or crosslinked molecule; and (3) physical blends of any of (1) and (2) and/or linear homopolymers.

DETAILED DESCRIPTION OF THE INVENTION

Particular examples of compounds of Formula A include the following:

1) Polyamides of Formula I:

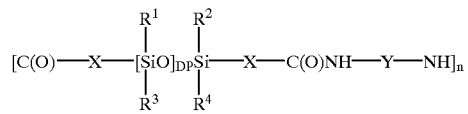

Formula I where the values for X, Y, n, $R^1$–$R^4$, and DP are as defined for Formula A. A particular subgroup of Formula I are compounds where each of $R^1$, $R^2$, $R^3$ and $R^4$ are each methyl. Preferred polyamides of Formula I are:

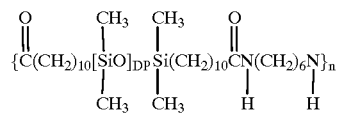

where DP is selected from 15–500, particularly 15–45, and even more particularly is 29. Another particular group contains polyamides of Formula I where the values of X, Y, DP and $R^1$–$R^4$ remain the same in each unit of the polymer.

2) Polyamides containing multiple siloxane block lengths as shown in Formula II:

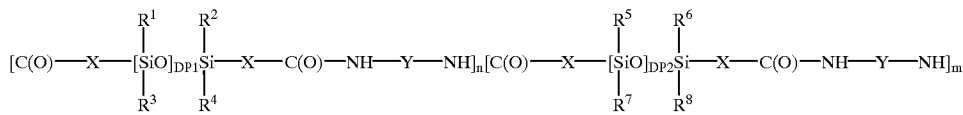

Formula II where X, Y, n, and $R^1$–$R^4$ have the meanings described above for Formula A; m is selected from the same groups as defined for n, and n and m denote the total number of units enclosed within the brackets, with the individual units arranged with regular, alternating, block or random sequencing; $R^5$–$R^8$ is selected from the same group as defined for $R^1$–$R^4$; DP I and DP2 may be the same or different and are each independently selected from the same group as defined for DP; and the units denominated by n and m may be structured to form either block (regularly sequenced) or random copolymers. A particular subgroup for compounds of Formula II has all of the R groups selected to be methyl. Another particular subgroup of compounds of Formula II has DP I=DP2. A third particular subgroup has all of the R groups selected to be methyl and DP1=DP2.

3) Polyamides synthesized from multiple diamines as shown in Formula III:

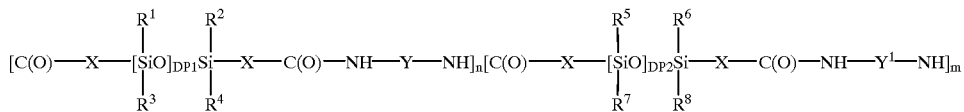

Formula III where X, Y, m, n, and $R^1$–$R^8$, DP1, DP2 have the same meanings as described above for Formula A and Formula II; $Y^1$ is independently selected from the same group as defined for Y; and the units denominated by n and m may be structured to form either block (regularly sequenced) or random copolymers. A particular subgroup of compounds of Formula III has DP1=DP2. Another particular subgroup of compounds of Formula III has all of the R groups selected to be methyl. A third particular subgroup has all of the R groups selected to be methyl and DP1=DP2.

4) Polyamides synthesized with trifunctional amine as shown in Formula IV:

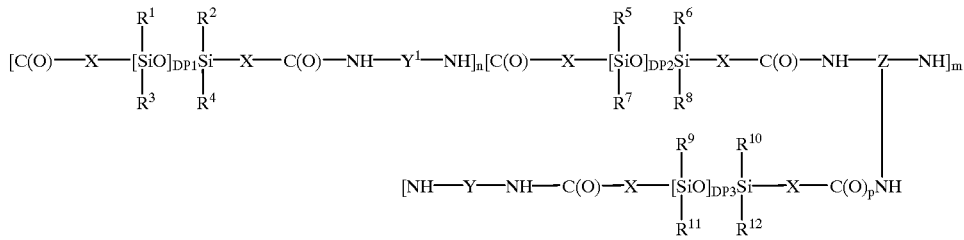

Formula IV where X, Y, $Y^1$, $R^1$–$R^8$, m, n, DP1–DP2, have the same values as defined above; $R^9$–$R^{12}$ are selected from the same group as defined for $R^1$–$R^8$, DP3 is selected from the same group as defined for DP; and p is selected from the same groups as defined for m and n; $Z=T(R^{20})(R^{21})(R^{22})$ where each of $R^{20}$, $R^{21}$ and $R^{22}$ are each independently selected from the group consisting of linear and branched C1–C10 alkylene, and T is selected from the group consisting of CR (where R is selected from hydrogen and the same group as defined for $R^1$–$R^4$), and a trivalent atom selected from N, P and Al. Preferred values for p are 1–25 with more preferred values being 1–7. Preferred values for $R^1$–$R^{12}$ are methyl. A preferred value for T is N. Particular values for each of DP1–DP3 are 15–500 and more particularly are 15–45. A preferred value for each of $R^{20}$, $R^{21}$ and $R^{22}$ is ethylene. A preferred value for Z=(—$CH_2CH_2$)$_3$N.

A particular group of compounds of Formula IV are

Formula IV

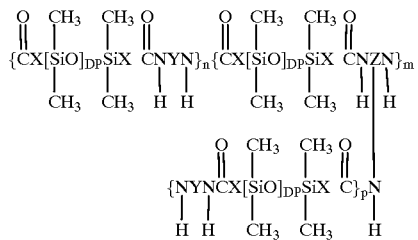

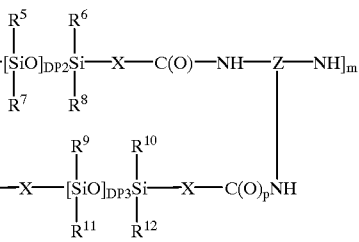

where X=—$(CH_2)_{10}$—, Y=—$(CH_2)$—; DP=15–45; m=5–20% of m+n+p; and Z=(—$CH_2CH_2$)$_3$N.

In general, the siloxane-based polyamides (1) contain both siloxane groups and amide groups to thicken compositions containing silicone fluids (volatile and/or non-volatile silicone fluids); (2) are non-flowable solids at room temperature; and (3) dissolve in a fluid which contains silicone at a temperature of 25–160 degrees C. to form a translucent or clear solution at a temperature in this range.

With regard to the siloxane units in the siloxane-based polyamides, the siloxane units must be in the main or backbone chain but can also optionally be present in branched or pendent chains. In the main chain the siloxane units occur in segments as described above. In the branched or pendent chains the siloxane units can occur individually or in segments.

Particular groups of siloxane-based polyamides include:

(a) polyamides of Formula I where DP is 15–50;
(b) physical blends of two or more polyamides wherein at least one polyamide has a value for DP in the range of 15–50 and at least one polyamide has a value for DP in the range of 30–500;
(c) compounds of Formula II where (1) the value for DP1=15–50 and the value for DP2=30–500 and (2) the portion of the polyamide having DP1 is about 1–99 weight % based on the weight of the total polyamide content and the portion of the polyamide having DP2 is about 1–99 weight %;
(d) physical blends of polyamides of Formula I made by combining (1) 80–99 weight % of a polyamide where n=2–10 and especially where n=3–6, and (2) 1–20 weight % of a polyamide where n=5–500, especially where n=6–100;
(e) polyamides of Formula m where at least one of Y and $Y^1$ contains at least one hydroxyl substitution;
(f) polyamides of Formula A synthesized with at least a portion of an activated di-acid (diacid chloride, dianhydride or diester) instead of the diacid;
(g) polyamides of Formula A where X=—$(CH_2)_3$—;
(h) polyamides of Formula A where X=—$(CH_2)_{10}$—;
(i) polyamides of Formula A where the polyamides are made with a monofunctional chain stopper selected from the group consisting of monofunctional amines, monofunctional acids, monofunctional alcohols, including fatty acids, fatty alcohols and fatty amines, such as, for example: octylamine, octanol, stearic acid and stearyl alcohol.

In general, the polyamides of Formula A can be produced through a condensation reaction in which a diacid is reacted with a diamine and water is removed. In this case the diacid contains siloxane groups. For example, carboxydecyl-terminated polydimethylsiloxane may be used as the diacid. Note that other organic diacids, diamines and monofunctional agents can be used in conjunction with the diacid and diamine to give modified properties. Also diacid chlorides, dianhydrides and diesters can be used instead of the diacids. One method includes using approximately equal molar amounts of the diamine and diacid.

A preferred reaction scheme for making polyamides of Formula I involves the condensation of a siloxane diacid with an organic diamine as follows:

(1) A dimethyl hydride endblocked polydimethylsiloxane is prepared containing the appropriate number of siloxane units to achieve the desired value of DP.

(2) The carboxylic acid group of undecylenic acid is protected through reaction with hexamethyldisilazane.

(3) The dimethyl hydride endblocked polydimethylsiloxane and the protected undecylenic acid (the products of Steps (1) and (2)) are reacted to produce a siloxane diacid (carboxydecyl terminated polydimethylsiloxane). This reaction is accomplished in the presence of a platinum catalyst such as chloroplatinic acid, and the product is washed with methanol to remove the trimethylsilyl protecting group.

(4) The siloxane diacid (product of Step (3)) is reacted with an organic diamine to produce a siloxane-based polyamide. This reaction may involve the use of reaction solvent such as toluene or xylene.

Optimal polymers are formed from the reaction of a siloxane diacid with a DP=1–500, especially 15–45, and an organic polyfunctional amine. Polymers having molecular weights in the range of 3,000–200,000 may be produced, especially those in the range of 5,000–50,000. Optimizing the length of the siloxane portions of the molecule (the "DP") involves a balancing of various considerations. Polyamides with long siloxane chains (for example, DP>50) tend to produce soft gels in cyclomethicone. The efficiency of the gellant is improved by reducing the length of the siloxane units (that is, selecting and making a molecule with a DP<50), but the compatibility with cyclomethicone may be compromised as the DP decreases. For example, a polyamide synthesized from a siloxane diacid with a DP=15 and hexamethylene diamine does not produce clears gels in cylcomethicone. However, transparent gels can be obtained if an organic emollient such as PPG-3 myristyl ether or isocetyl alcohol is blended at various levels with the silicone fluids. As a result, polymers with DP=30 are preferred, so that the formulation for the resulting cosmetic composition has a combination of compatibility with silicone fluids and good gelling efficiency.

Preferred organic amines include (1) linear alkyl diamines such as hexamethylene diamine and ethylene diamine and mixtures thereof; (2) phenylene diamine; and (3) other amines such as piperizine, decamethylene, xylene diamine, and polyethylene glycol diamine.

Acceptable variations of this process may be used by:

(a) Varying the length of the individual siloxane portion (the DP of the siloxane diacid), noting that higher DP values lead to better polymer compatibility with silicone fluids, but lowered gelation efficiency and, hence, softer gels;

(b) Optimizing the reaction conditions to promote a selected range of molecular weights, for example, higher molecular weights. It is believed that higher molecular weight polymers provide gels with better mechanical properties; such higher molecular weight distributions could be obtained through minimizing reagent impurities, optimizing reaction times and temperatures, etc. Examples of removing impurities include removing monofunctional impurities such as those in the carboxy silicones.

(c) Varying the diamine used to alter the rigidity of gels produced. Substituted diamines such as trimethyl hexylene diamine produce polymers with lower gelation efficiency than polymers based on analogous unsubstituted diamines (such as hexamethylene diamine). It is believed that diamines with steric hindrance act to interrupt the intermolecular associations of the polymer and, thus, result in softer gels.

(d) Selecting a solvent other than toluene or xylene to be used as a reaction solvent The solvent should be chosen based on its boiling point, its ability to form azeotropes with water, and its safety profile. Optimal solvents will facilitate elimination of water from the reaction vessel to favor higher molecular weight products. Alternatively, cyclomethicone can be used as a reaction solvent so that a gel system is created directly in situ.

(e) Replacing the siloxane diacid (also called silicone diacid) reagent with an analogous activated species such as an ethyl diester, di-acid chloride or di-anhydride, to improve efficiency.

(f) Replacing the organic diamine in part with an organic triamine or a higher amine to produce a branched or crosslinked polyamide.

A particular example of this general reaction scheme is the use of undecylenic acid (10-undecanoic acid, CAS #112-38-9) and di(trimethylsilyl)amine as the protecting group on the undecylenic acid.

A more particular description of the overall process is as follows. The first step involves the preparation of a dimethylhydride endblocked polydimethyl siloxane polymer using acid catalysis. Dihydrido tetramethyldisiloxane, dimethylcyclosiloxanes and trifluoromethane sulfonic acid are mixed together and heated to 80 degrees C. to allow for an equilibration reaction which forms the dimethylhydrogen endblocked polydimethyl siloxane polymer and dimethylcyclosiloxanes. After 4 hours of polymerizing at 80 degrees C., the siloxane is neutralized using calcium carbonate or sodium bicarbonate at 80 degrees C. for a minimum of 2 hours. Once neutralized the polymer is filtered and isolated (Product A).

The carboxylic acid group of undecylenic acid is protected by a trimethylsilyl group which is obtained by reacting undecylenic acid with hexamethyldisilazane. Undecylenic acid and toluene are added to a flask and the hexamethyldisilazane is added to an addition funnel and added dropwise while the materials are mixing. Upon complete addition of the hexamethyldisilazane, the temperature of the reaction vessel is increased to 110 degrees C. and the mixture is allowed to react for four hours. The flask is then heated to 150 degrees C. under a vacuum in the range of 5–20 mm of mercury and the toluene is removed. After complete removal of the toluene, a distillation column is used to purify the protected undecylenic acid. The distillation is performed at approximately 150 degrees C. and 10 mm Hg. The overhead product is isolated (Product B).

Product A is reacted with Product B via a hydrosilylation reaction using any suitable platinum or rhodium catalyst. Product A is placed in a flask with the platinum catalyst, the materials are mixed and heated to 80 degrees C. With regard to an example of a suitable catalyst, a sufficient amount of a neutralized complex of platinous chloride and divinyl tetramethyl disiloxane (for example as described in U.S. Pat. No. 5,175,325) may be used at a concentration to provide 5–15 parts per million (ppm) Pt metal per total composition. Product B is placed in an addition funnel and added dropwise to product A at a controlled rate to control the exotherm which results. An exotherm occurs so it is important to monitor the addition of Product B. After the addition of Product B is completed, the mixture is allowed to react at temperature for an additional hour. The mixture is then heated to 150 degrees C. under vacuum (for example, in the range of 5–20 mm of mercury) to remove dimethylcyclosiloxanes and any unreacted undecylenic acid. The mixture is then cooled to below 60 degrees C. and methanol is added to deprotect the undecylenic acid. This reaction forms the carboxylic acid endblocked siloxane and trimethylmethoxy silane. The materials are allowed to react for at least one hour at 60 degrees C. and then the flask is heated to 150 degrees C. under vacuum (for example, in the range of 5–20 mm of mercury) to remove residual methanol and trimethylmethoxy silane. The dicarboxylic acid functional siloxane is then isolated (Product C).

Product C is reacted with hexamethylenediamine in an amidization reaction. Product C and toluene are placed in a flask and allowed to mix at room temperature. Hexamethylenediamine is added to Product C and the temperature of the flask is increased to 150 degrees C. The flask is equipped with a Dean Stark trap and a nitrogen purge to assist in the water removal to form the amide linkage. Once at 150 degrees C., the reaction is allowed to proceed for 3–4 hours; toluene and water are removed from the Dean Stark trap periodically. After complete reaction the product is removed from the reaction vessel while still molten. Upon cooling the silicone polyamide forms a clear rigid thermoplastic (Product D).

Compounds of Formula I may be made by using a siloxane diacid (or acid derivative) with a single average DP value.

Compounds of Formula II may be made by using two or more dimethylhydrogen endblocked siloxanes which are prepared, then mixed and converted to carboxylate, and then converted to a polyamide having a random sequence. Optionally, the two (or more) dimethylhydrogen endblocked siloxanes may be added sequentially to form a block copolymer.

Compounds of Formula III may be made as described above in the particular process description, but the diamines are mixed and then added to the siloxane diacid (or acid derivative) to form the polyamide. Optionally they may be added sequentially to form different blocks.

Compounds of Formula IV may be made as described above in the particular process description, but the polyamine is mixed with the diamine then added to the diacid (or acid derivative as described above).

It has been found that optimal gelation occurs with polyamide gellants of molecular weight (number average) greater than 4,000 daltons as determined by gel permeation chromatography (GPC) using polydimethylsiloxane as a standard. Polymers of extremely high molecular weight (for example, greater than 200,000 daltons) tend to produce rubbery, elastic gels and are less desirable and the optimal range of molecular weights for the primary gellant should be from 4,000–50,000 daltons, especially 5,000–50,000 daltons. It is believed, however, that incorporation of low levels of such high molecular weight species, for example, 0.5 weight % of a high molecular weight polyamide having a molecular weight in the range of 20,000–200,000 may give the base composition and cosmetic compositions made therefrom improved mechanical properties.

Optionally the polyamide gelling agent can also be endcapped. The endcapping may be effected with the use of an agent selected from the group consisting of C1–C20 aliphatic monohydric alcohols, C1–C20 aliphatic primary amines, phenyl primary amines optionally substituted by 1–3 members selected from C1–C6 aliphatics, C1–C20 aliphatic acids and C1–C20 aliphatic acid chlorides.

As noted above, the siloxane-based polyamides used as thickening agents in base and cosmetic compositions of the present invention contain both siloxane units and amide linkages. The siloxane units provide compatibility with the silicone fluid (for example with the cyclomethicones), while the amide linkages and the spacing and selection of the locations of the amide linkages facilitate gelation and the formation of cosmetic products. While opaque as well as clear compositions may be formed, it is preferred that the cosmetic compositions formed be clear and leave no residue upon cooling a solution of the siloxane polymer in the silicone fluid.

The base composition formed from the polyamides of this invention and the silicone fluids (including volatile and non-volatile silicone fluids) (optionally with the addition of other solvents and/or other cosmetic additives) can be made by techniques of mixing and heating known to those skilled in the art for making such forms as gels, soft solids and sticks as well as making cosmetic products which contain various active ingredients.

The base compositions according to the present invention include (1) at least one silicone fluid; (2) a siloxane-based polyamide gelling agent containing a siloxane portion in the backbone which is a polymer that is soluble in the silicone fluid and that can form a gel from a solution in the silicone fluid; and (3) optionally at least one additional solvent (for example, that is miscible in the silicone fluid chosen).

By silicone fluid is meant those materials conventionally utilized in cosmetic compositions. Suitable silicone fluids may be volatile, non-volatile or a mixture of both. These include linear siloxanes known as dimethicones, linear siloxanes containing an aromatic substitution such as phenyl trimethicone and the various cyclic siloxanes having from 4–6 siloxane units in a ring optionally substituted by C1–C6 alkyl or phenyl, particularly cyclic dimethyl siloxanes such as cyclomethicones. Mixtures of such silicone fluids may also be used. Suitable volatile silicone liquids are described in U.S. Pat. No. 5,102,656 to Kasat, referenced above. Examples of other known silicone fluids for use in cosmetic compositions are disclosed in U.S. Pat. No. 4,853,214 to Orr, referenced above and are suitable for use in this invention. Other particular examples include linear volatile silicone fluids, for example, silicone liquids conventionally used in cosmetic compositions.

By soluble in the silicone fluid, we mean that the polymer can be dissolved in the silicone fluid at least at elevated temperatures but below the boiling point of the silicone fluid.

The base composition is then combined with at least one active ingredient (which itself may need a further vehicle to be incorporated into the base composition) and other optional ingredients such as fragrance, emollients (especially silicone-miscible emollients), coloring agents, fillers, antibacterials (antimicrobials) and other conventional ingredients known to those in the art for formulating such products to form cosmetic compositions.

The cosmetic compositions according to the present invention include at least one silicone fluid and the siloxane-containing polymer as well as at least one cosmetically active material, incorporated in the composition in an amount sufficient to have a functional effect Such actives include, but are not limited to fragrances, sunscreens, antiperspirants, deodorants and antibacterials (antimicrobials). For example, where the composition is a composition to protect skin from the sun, a sufficient amount of a sun-screening agent is provided in the composition such that when the composition is applied to the skin, the skin is protected from the harmful effects of the sun (for example, is protected from ultraviolet rays from the sun).

The compositions of the present invention can also be utilized to form clear antiperspirant compositions having multiphase systems, such multiphase systems having a polar (for example, water) phase (including an antiperspirant active material) and an oil phase (including the silicone fluids and siloxane polymer). In order to provide a clear multiphase system, refractive indices of the oil and polar phases desirably should be matched, as done conventionally in the art.

Base and cosmetic compositions according to the present invention can easily be manufactured by methods known to those skilled in the art such as by using known mixing procedures. Base compositions according to the present invention can be made by mixing the various components at an elevated temperature (that is, by heating and mixing the various components) and then cooling in order to form the gelled (solidified) composition, for example, as a gel or stick. For cosmetic compositions, the additional ingredients are added using techniques and at times in the manufacturing process as are known to those in the art. Desirably, any volatile components (such as fragrances) are added to the mixture at a relatively late stage of the mixing, so as to limit volatilization of the volatile components.

Generally, the solvent and thickening agent (for example, the polyamide gelling agent) are mixed and heated so as to fully dissolve the thickening agent in the solvent. An active ingredient (for example, antiperspirant active material, for example, in dry form or as part of a solution) can be added after the thickening agent fully dissolves, and mixing then takes place. Mixing continues with cooling, with, for example, colorant and fragrance then being added. Thereafter, the resulting composition, still liquid, is poured into canisters, for example, dispensing packages, and solidified, as with conventional stick and gel compositions.

An illustrative and non-limiting example of the present invention is as follows. The silicone-based polyamide polymer can be dissolved in the silicone fluid, for example, at elevated temperatures (for example, up to 160 degrees C.) so as to form a solution, with cooling then being performed to form the gel. It is preferred that the solution is not heated too long or at too high a temperature, since such disadvantageously may cause the gel to be colored (rather than colorless). The cosmetic active can be added to the solution of silicone fluid and polymer gelling agent and mixed therewith so as to be homogeneously distributed in the product.

For example, the silicone fluids and siloxane-containing polymers can be mixed at elevated temperatures so as to dissolve the polymer in the silicone fluids, with cosmetically active ingredients being added to the mixture of silicone fluids and polymer. Upon cooling the mixture, the polymer forms a gel from the mixture, achieving the desired product. In the case where an aqueous phase is included, an emulsion is the result. The base compositions of the present invention are thermally reversible gels; that is, they form gels upon being cooled and are liquified when heated.

Where the product is a stick product, the molten product, at elevated temperatures, can be poured into dispensing containers and allowed to cool and harden therein. Where the product is a soft solid or cream, the product can be packaged into conventional dispensing containers having a porous top surface, as conventionally done in the art.

When a cosmetic composition according to the present invention is in the form of a stick product, the composition can be applied by elevating the stick out of the package so as to expose the end of the stick, and then rubbing the end of the stick on the skin in order to deposit stick material (including the cosmetically active material such as the antiperspirant active) on the skin. When the composition according to the present invention is in the form of a gel composition, packaged in a dispensing container having a top surface with pores, the gel is extruded from the dispensing container through the pores and applied to the skin by rubbing the gel material that has been extruded through the top surface of the container on the skin. Thus, in the case of an antiperspirant, the active material on the skin is available to reduce body malodor and/or reduce the flow of perspiration from, for example, the axillary regions of the body.

Polyamides of this invention can be used as a thickening agent in compositions containing silicone fluids to form creams (for example, semi-solid or soft solid), gels and sticks; thus, both soft (and mushy) or firm (and hard) compositions can be formed. The firmness of the product will depend on the amount of the gelling agent(s) used.

Products of varying clarity and transparency can be formed. Clear cosmetic compositions can be formed if all the components of the particular cosmetic composition are soluble in each other, resulting in a single phase product. Clear cosmetic compositions can also be prepared from multiple phase compositions, for example, an emulsion or suspension, if each phase individually is clear and the refractive index of each phase is matched. Additionally, clear cosmetic compositions can be made from multiple phase compositions if the droplet (particle) size of the internal phase(s) are small enough, less than 0.5 micron. Examples of this are microemulsions and very fine particles in suspension. If the aforementioned conditions are not met, the cosmetic compositions will exhibit various degrees of transparency and opacity.

Additives may be added to the base composition to add active ingredients, improve mechanical properties, improve aesthetic properties, make a clear product, make a product with color, etc. Thus, cosmetic compositions may then be made by combining the base composition with one or more additional components, active ingredients, one or more vehicles to allow the active ingredient to combine more easily (or with more desirable properties) with the base composition, and other ingredients used by those in the art to formulate cosmetically acceptable products including fragrances, emollients, antibacterials hardeners, strengtheners, chelating agents, colorants, emulsifiers and other additives such as, silicas, silica-based resins, corn starch, alumina, fumed silica, calcium carbonate, clay, talc, high molecular weight polymers (for example silicone gums, elastomers, polymethylmethacrylate, polyethylene, polypropylene and polytetrafluoroethylene).

In the case of antiperspirant emulsion or suspension formulations, there is an external gelled oil phase and an internal phase which contains the antiperspirant active. The external gelled oil phase contains silicone fluids and the siloxane-based polyamide gellant, as well as optional additives for the antiperspirant product such as emollients, surfactants, fragrances, etc.

In the suspension approach the internal, antiperspirant active phase consists of solid particles. These particles may be antiperspirant salt powders (such as aluminum chlorohydrate or aluminum zirconium tetrachlorohydrex glycine) and may contain water levels of 0–75 weight %. At the higher water levels (for example, >50% water) some gelation promoter (such as ammonium acetate) may be required to provide rigidity to these aqueous droplets.

In the emulsion approach the internal phase consists of a liquid solution containing dissolved antiperspirant salt, and typically involves solvents such as water, propylene glycol, dipropylene glycol, tripropylene glycol, ethanol, etc.

Microemulsions can also be used to achieve clear products.

In one particular aspect of the invention, deodorant and/or antiperspirant compositions, in the form of creams (including soft solids and semi-solids), gels and also sticks, which have high efficacy, an attractive appearance (for example, which can be clear or at least translucent), and preferably which are made to leave substantially no visible (white) residue either upon application or upon drying, can be achieved.

In the base composition, the polyamide gelling agent can be used in an amount of 0.5–80 percent by weight, more particularly 1–30 percent by weight and most particularly 2–20 percent by weight. It is preferred that the gellant not exceed 50 percent by weight of the base composition. The silicone fluid portion is in the range of 5–95 percent by weight, more particularly 10–80 percent by weight, even more particularly 20–80 percent by weight. Optionally, additional solvents, mixtures of solvents or cosmetic additives may be added to the base composition. Suitable additional solvents are those which are either themselves or in mixtures with other solvents miscible in the originally selected silicone fluid (for example, C14–C20 fatty alcohols, isopropyl myristate, and PPG-3 myristyl ether).

Thus, for gels an addition level of 0.5–8 weight %, preferably 2–6%, based on the total weight of the cosmetic composition may be used.

For sticks, higher levels of the silicone-based polyamide will be used such as in the range of 5–30, particularly 6–20 and, more particularly, 10–15 weight percent based on the total weight of the composition.

The siloxane-based polyamide gelling agent, can consist of one or more polyamides as described above (or a mixture of these polymers) as the sole gelling agent, or can contain the polyamide admixed with other thickening agents (including conventional gelling agents). The siloxane units provide compatibility with the silicone fluids. The amide portions are utilized reversibly for cross-linking purposes so as to form the gel.

Compositions according to the present invention are thermoreversible gels; that is, the gels are formed by cooling a solution of the polymer in the silicone fluids, but the gel can be broken (formed back into a liquid) by heating the gel.

The gels of the present invention include silicone fluids. These fluids can be volatile or non-volatile and include, illustratively (and not of a limiting nature), phenyl trimethicone, cyclomethicones and/or dimethicones. Preferably, the silicone fluid includes cyclomethicones. The cyclomethicone used (that is, ring size of the cyclomethicone) has an effect on the hardness of the gels formed. That is, cyclomethicone having five siloxane units produces a softer gel than that produced utilizing a material with 6 siloxane units. As the ring size of the cyclomethicone increases, the rigidity of the gel system formed increases. As described above, particular examples of suitable cyclomethicones include those having rings of 4–6 siloxane units.

The base composition is then mixed with the other ingredients listed elsewhere so that the final cosmetic composition can be made. Such additional ingredients can be used in amounts of 0.1–85 percent, more particularly 0.1–75 percent and, even more particularly, 0.1–55 percent where the percentages are based by weight on the total composition as 100 percent. The lower percent ranges include formulations where only fragrances or antimicrobials are used, and the upper ranges include formulations containing active antiperspirant ingredients. An antiperspirant active itself (excluding any vehicle for adding the active to the formulation) can be present in the final cosmetic formulation in an amount of from 5–30 percent.

Cosmetic compositions according to the present invention can also include surface active agents and/or solvents for the cosmetically active material. For example, where the composition is an antiperspirant composition, containing antiperspirant active material, the antiperspirant active material can be included in the composition in a solution in, for example, water, ethanol and/or propylene glycol, which may not be miscible with the silicone fluid, and the composition can also include surface active agents so as to disperse the solution of antiperspirant active material in the composition. Where the composition according to the present invention is a deodorant composition, the composition can include conventional fragrances and/or antibacterial (antimicrobial) agents as deodorant active materials.

Various cosmetically active materials incorporated in cosmetic compositions are disclosed in U.S. Pat. No. 4,322,400 to Yuhas, the contents of which are incorporated herein by reference in their entirety.

Throughout the present specification, "antiperspirant active" and "deodorant active" materials are discussed. Both types of materials contribute to reduction of body malodor, for example, axillary malodor. By reduction of body malodor, it is meant that, generally, there is less body malodor after application of the composition to a person's skin, as compared to a person's malodor without application of the composition. Such reduction can be due to a masking of the malodor, absorption and/or chemical reaction of the malodorous material, reduction of the levels of the bacteria producing the malodorous materials, for example, from perspiration, reduction of perspiration, etc. The antiperspirant active materials, when utilized in appropriate amounts, primarily act to reduce malodor by reducing perspiration; the antiperspirant active materials can also have a deodorant function, for example, as an antimicrobial or bacteriostatic agent. The deodorant active materials do not substantially reduce perspiration, but reduce malodor in other ways. For example, as fragrances masking the malodor or reducing the malodor intensity; absorbents; antimicrobial (bacteriostatic) agents; or agents chemically reacting with malodorous materials.

Where the composition contains an antiperspirant active, any of the known antiperspirant active materials can be utilized. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention.

Antiperspirant actives can be incorporated into compositions according to the present invention in amounts in the range of 0.1–30%, preferably 15–25%, by weight, of the total weight of the composition. The amount used will depend on the formulation of the composition. For example, at amounts in the lower end of the broader range (for example, 0.1–10%), the antiperspirant active material will not substantially reduce the flow of perspiration, but will reduce malodor, for example, by acting as an antimicrobial material.

Where deodorant active materials are incorporated in compositions according to the present invention, so as to provide deodorant compositions, conventional deodorant fragrances and/or antimicrobial agents can be incorporated as the deodorant active materials. A fragrance would, illustratively, be incorporated in an amount of 0.5%–3.0% by weight, of the total weight of the composition. Known bacteriostats include bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl) urea (Triclocarban) and various zinc salts (for example, zinc ricinoleate). The bacteriostat can, illustratively, be included in the composition in an amount of 0.1–1.0% by weight, of the total weight of the composition. Triclosan, can illustratively be included in an amount of from 0.1% to about 0.5% by weight, of the total weight of the composition.

Compositions according to the present invention can include other cosmetic additives conventionally incorporated in cosmetic compositions, including (but not limited to) perfumes, cosmetic powders, colorants, emulsifiers, emollients, waxes, organosilicones, fatty esters, fatty alcohols, bees wax, behenoxy dimethicone, stearyl alcohol, etc. and other cosmetic agents. As for various other ingredients which can be incorporated, attention is directed to the optional components such as colorants, perfumes and additives described in the following U.S. patents: U.S. Pat. No. 5,019,375 to Tanner, et al (the contents of which are incorporated herein by reference in their entirety); U.S. Pat. No. 4,937,069 to Shin (the contents of which are incorporated herein by reference in their entirety); and U.S. Pat. No. 5,102,656 to Kasat (the contents of which have been previously been incorporated herein by reference in their entirety). The use of optional additives may, of course, adversely affect clarity.

Where the composition is an antiperspirant composition, the composition can also include a solvent for the antiperspirant active. This solvent, which is not miscible with the silicone fluid, can illustratively be water, ethanol, propylene glycol and/or dipropylene glycol. Where the antiperspirant active is utilized in a solution in the solvent, it may be necessary to match refractive indices of the antiperspirant active solution with that of the oil portion of the composition, in order to achieve a transparent or clear composition. Where the antiperspirant active material is suspended in the base composition as particulate material, it may also be necessary to match refractive indices of the active material and base composition to obtain a clear or transparent composition as described above. Such refractive index matching is a technique known in the art, and is shown in PCT (International Application) Publication No. WO 92/05767, the contents of which have previously been incorporated herein by reference in their entirety. The solvent for the antiperspirant active material can be included in the composition in an amount within the range of 0–75%, preferably 0–25%, by weight, of the total weight of the composition.

The solvent for the thickening agent is included in the composition in an amount sufficient such that the thickening agent can be dissolved therein and gelled therefrom, and includes a silicone fluid (for example, a silicone oil, such as cyclomethicone and/or dimethicone). Thus, the thickening agent can be dissolved in the solvent and gelled therefrom, for example, upon cooling the composition during manufacture thereof. The solvent is not limited to those materials containing only a silicone fluid, and can contain other solvents for the thickening agent as long as such other solvents are compatible with, for example, the active cosmetic material and do not disadvantageously affect, for example, clarity of the composition, especially where it is desired to provide a clear cosmetic composition. Illustratively, and not to be limiting, the solvents can include esters (for example, isopropyl myristate and C12–15 alkyl lactate), silicone fluids (for example, cyclomethicone, dimethicone), guerbet alcohols having 8–30 carbons, particularly 12–22 carbons (for example, isolauryl alcohol, isocetyl alcohol, isostearyl alcohol), fatty alcohols (for example, stearyl alcohol, myristyl alcohol, oleyl alcohol), ethanol, and ethoxylated and propoxylated alcohols (for example, the polyethylene glycol ether of lauryl alcohol that conforms to the formula $CH_3(CH_2)_{10}CH_2(OCH_2CH_2)_b$ OH where b has an average value of 4 (also called laureth-4). PPG-14 butyl ether, where the "PPG-14" portion is the polymer of propylene oxide that conforms generally to the formula $H(OCH_2C(CH_3)H)_cOH$, where c has an average value of 14, or PPG-3 myristyl ether which is the polypropylene glycol ether of myristyl alcohol that conforms to the formula $CH_3(CH_2)_{12}CH_2(OCH(CH_3)CH_2)_dOH$ where d has an average value of 3. Mixtures of solvents can also be used. Of course, the gelling agent must be soluble in the solvent system, at least at elevated temperatures, as described in U.S. Pat. No. 5,500,209.

Compositions according to the present invention desirably include silicone-miscible emollients. Illustrative emollients, which are not limiting of the present invention, would include guerbet alcohols (such as isocetyl alcohol or isostearyl alcohol); esters (such as isopropyl palmitate, isopropyl isostearate, octyl stearate, hexyl laurate and isostearyl lactate); a liquid mixture of hydrocarbons which are liquids at ambient temperatures (such as petroleum distillates and light mineral oils); and ethanol. The silicone-miscible solvents (also called emollients) can be included in the compositions of the present invention in amounts within the range of 0–70%, preferably 0–25%, by weight, of the total weight of the composition.

Where a multi-phase system is utilized as the composition of the present invention, preferably the composition includes a surfactant or surfactant blend. Surfactants illustratively include alkanolamides (such as N-alkyl pyrrolidone), ethoxylated amides (for example, the polyethylene glycol amide of tallow acid that conforms generally to the formula RC(O)—NH—(CH$_2$CH$_2$O)$_n$H where RCO— represents the fatty acids derived from tallow and n has an average value of 50 (also called PEG-50 tallow amide)); amine oxides (for example, cocamidopropylamine oxide); ethoxylated carboxylic acids (for example, the polyethylene glycol diester of lauric acid that conforms generally to the formula CH$_3$(CH$_2$)$_{10}$C(O)—(OCH$_2$CH$_2$)$_n$O—C(O)(CH$_2$)$_{10}$CH$_3$ where n has an average value of 8 (also called PEG-8 dilaurate)); ethoxylated glycerides (for example, a polyethylene glycol derivative of Castor Oil with an average of 4 moles of ethylene oxide (also called PEG4 castor oil)); glycol esters (for example, propylene glycol ricinoleate); monoglycerides (for example, glycerol myristate); polyglyceryl esters (for example, polyglyceryl4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated alcohols (for example, laureth-4); ethoxylated lanolin (for example, a polyethylene glycol derivative of Lanolin with an average of 20 moles of ethylene oxide (also called PEG-20 lanolin)); ethoxylated polysiloxanes (for example, dimethicone copolyol); propoxylated polyoxyethylene ethers (for example, the polyoxypropylene, polyoxyethylene ether of cetyl alcohol that conforms generally to the formula CH$_3$(CH$_2$)$_{14}$CH$_2$(OCH(CH$_3$)CH$_2$)$_x$(OCH$_2$CH$_2$)$_y$OH where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula R—NH—(CH$_2$CH$_2$O)$_n$H (also called PEG-15 tallow amine)) or anionic (for example, sodium lauroyl isethionate which is the sodium salt of the lauric acid ester of isethionic acid) surfactants.

The surfactant or blend thereof incorporated in compositions according to the present invention can, illustratively, be included in amounts of 0–15%, preferably 1–10%, by weight, of the total weight of the composition.

As indicated previously, the compositions according to the present invention can be creams (semi-solids or soft-solids), gels or sticks, depending on amounts of thickening agent incorporated in the composition. It is difficult to quantitatively distinguish between a cosmetic "gel" and a cosmetic "stick". Generally, a gel is more viscous than a liquid or than a paste which fails to retain its shape; however, it is not as rigid as a stick. Typically, it is understood that gels are soft, deformable products while sticks are free-standing solids. For example, by rheological analysis, a commercial deodorant stick has been determined to have a plateau storage modulus G'(ω) of roughly 10$^5$ Pa and a complex viscosity of 10$^6$ Pa second (both at an angular frequency of 0.1 rad-sec). On the other hand, a commercial antiperspirant gel has been determined to have a G'(ω) value of roughly 10$^3$ Pa and a complex viscosity of 10$^4$ Pa second (at 0.1 rad-sec).

Cosmetic compositions according to the present invention include both a thickening agent and a solvent for the polyamide gelling agent (in the present application, the polyamine gelling agent and solvent for the gelling agent provide a vehicle for the active cosmetic material, and have been so designated as a vehicle).

In a series of preferred embodiments base compositions and cosmetic compositions according to the present invention contain a sufficient amount of the thickening agent such that the final cosmetic composition is a solid composition, for example, a gel or stick.

In the following, illustrative examples of compositions within the scope of the present invention are set forth. These examples are illustrative of the present invention, and are not limiting. Amounts of components in these examples are in weight percent, of the total weight of the composition.

The cosmetic composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Where a gel or soft-solid cosmetic composition is produced, the composition can be introduced into a dispensing package (for example, a package having a top surface with pores) as conventionally done in the art. Thereafter, the product can be dispensed from the dispensing package as conventionally done in the art, to deposit the active material, for example, on the skin. This provides good deposition of the active material on the skin.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

Throughout the specification and claims all percents are in percents by weight.

A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectro-photometer. As to this definition of clear, see European Patent Application Publication No. 291,334 A2. Thus, according to the present invention, there are differences between transparent (clear), translucent and opaque compositions.

In a particular embodiment of the invention a polyamide is used to form a solid composition of the present invention which is a clear, or at least a translucent, gel or stick (for example, antiperspirant gel or stick composition).

In the following, specific synthesis examples for forming siloxane-based polyamides of this invention are set forth, and specific examples of antiperspirant and deodorant compositions within the scope of the present invention are also set forth. These specific synthesis examples and examples are illustrative in connection with the present invention, and are not limiting. In the following, as well as throughout the present disclosure, names utilized are the CTFA (Cosmetics, Toiletry and Fragrance Association, Inc.) names, as set forth in the *CTFA International Cosmetic Ingredient Dictionary* (4th Ed. 1991), the contents of which dictionary are incorporated herein by reference in their entirety. Throughout the description of this invention chemical abbreviations and symbols have their usual and customary meanings. Unless otherwise indicated, the vacuums described in Examples 1–5 are in the range of 5–20 millimeters of mercury. While particular siloxane-based polyamides are disclosed or used in the following Examples, it is to be understood that other siloxane-based polyamides (for example, those made with a purified siloxane diacid, di-anhydride, diesters, or diacid chloride) may also be used and are within the spirit and scope of the invention.

EXAMPLES 1–5
Preparation of Siloxane-based Polyamides

Example 1

A 3000 ml three neck flask equipped with a thermometer, electrical stirrer and a condenser was charged with 1427.2 g of dimethylcyclosiloxanes, 172.8 g of tetramethyldihydrogen disiloxane and 1.3 g of trifluoromethane sulfonic acid. The flask was heated to 80 degrees C. and kept at this temperature for 4 hours. After 4 hours, 25 g of sodium bicarbonate were added and the contents of the flask were mixed at 80 degrees C. for another 2 hours. The reaction product (15 DP dimethylhydrogen endblocked polydimethyl siloxane) was filtered using a 0.8 micron filter paper. To a 2000 ml flask equipped with a thermometer, electrical stirrer, condenser and nitrogen purge were added 800 g of the product (15 DP dimethylhydrogen endblocked polydimethyl siloxane) and a sufficient amount of a neutralized complex of platinous chloride and divinyl tetramethyl disiloxane was added to provide a concentration of 5–15 ppm Pt metal per total composition. The mixture was heated to 80 degrees C. while mixing. In an addition funnel were placed 325.0 g of trimethylsilyl protected undecylenic acid; the material was added dropwise to the reactor and an exotherm was observed. After complete addition the temperature was increased to 110 degrees C. and the mixture was allowed to react for an additional hour. The temperature was then raised to 150 degrees C. under a vacuum for approximately 1 hour. The vacuum was removed and the reactor was allowed to cool below 60 degrees C. Once below 60 degrees C., 110.0 g of methanol were added to the reactor and the temperature set at 60 degrees C. After 2 hours the temperature was increased to 150 degrees C. under vacuum to remove residual methanol and trimethylmethoxysilane. To a 500 ml flask equipped with a thermometer, electrical stirrer, condenser, nitrogen purge and a Dean Stark trap were added 100 g of the product (15 DP carboxylic acid endblocked siloxane), 20 g of toluene and 7.19 g of hexamethylenediamine. The reactor temperature was increased to 150 degrees C. for 4 hours. During the reaction water and toluene were periodically removed from the Dean Stark trap. The final silicone polyamide was poured off at approximately 150 degrees C. while still in the melt form.

Example 2

A 3000 ml three neck flask equipped with a thermometer, electrical stirrer and a condenser was charged with 2000.0 g of dimethylcyclosiloxanes, 129.9 g of tetramethyldihydrogen disiloxane and 1.6 g of trifluoromethane sulfonic acid. The flask was heated to 80 degrees C. and kept at temperature for 4 hours. After 4 hours, 45 g of calcium carbonate were added and mixed at 80 degrees C. for another 2 hours. The reaction product was filtered using a 0.8 micron filter paper. To a 2000 ml flask equipped with a thermometer, electrical stirrer, condenser and nitrogen purge were added 816 g of the product (30 DP dimethylhydrogen endblocked polydimethyl siloxane) and sufficient of the platinum catalyst as described in Example 1. The mixture was heated to 80 degrees C. while mixing. In an addition funnel were placed 189.0 g of trimethylsilyl protected undecylenic acid; the material was added dropwise to the reactor and an exotherm was observed. After complete addition the temperature was increased to 110 degrees C. and allowed to react for an additional hour. The temperature was then taken to 150 degrees C. under a vacuum for approximately 1 hour. The vacuum was removed and the reactor was allowed to cool below 60 degrees C. Once below 60 degrees C., 57.1 g of methanol were added to the reactor and the temperature set at 60 degrees C. After 2 hours the temperature was increased to 150 degrees C. under vacuum to remove residual methanol and trimethylmethoxysilane. To a 500 ml flask equipped with a thermometer, electrical stirrer, condenser, nitrogen purge and a Dean Stark trap were added 250 g of the product (30 DP carboxylic acid endblocked siloxane), 40 g of toluene and 10.9 g of hexamethylenediamine. The reactor temperature was increased to 150 degrees C. for 4 hours. During the reaction water and toluene were periodically removed from the Dean Stark trap. The final silicone polyamide was poured off at approximately 150 degrees C. while still in the melt form.

Example 3

A 2000 ml three neck flask equipped with a thermometer, electrical stirrer and a condenser was charged with 1394.4 g of dimethylcyclosiloxanes, 5.6 g of tetramethyldihydrogen disiloxane and 0.67 g of trifluoromethane sulfonic acid. The flask was heated to 80 degrees C. and kept at temperature for 4 hours. After 4 hours, 35 g of calcium carbonate were added and mixed at 80 degrees C. for another 2 hours. The reaction product was filtered using a 0.8 micron filter paper. To a 2000 ml flask equipped with a thermometer, electrical stirrer, condenser and nitrogen purge were added 1200 g of the product (500 DP dimethylhydrogen endblocked polydimethyl siloxane) and sufficient of the platinum catalyst as described in Example 1. The mixture was heated to 80 degrees C. while mixing. In an addition funnel was placed 16.5 g of trimethylsilyl protected undecylenic acid, the material was added dropwise to the reactor, an exotherm was observed. After complete addition the temperature was increased to 110 degrees C. and allowed to react for an additional hour. The temperature was then taken to 150 degrees C. under a vacuum for approximately 1 hour. The vacuum was removed and the reactor was allowed to cool below 60 degrees C. Once below 60 degrees C., 30.0 g of methanol were added to the reactor and the temperature set at 60 degrees C. After 2 hours the temperature was increased to 150 degrees C. under vacuum to remove residual methanol and trimethylmethoxysilane. To a 2000 ml flask equipped with a thermometer, electrical stirrer, condenser, nitrogen purge and a Dean Stark trap were added 988.5 g of the product (500 DP carboxylic acid endblocked siloxane), 75 g of toluene and 3.07 g of hexamethylenediamine. The reactor temperature was increased to 150 degrees C. for 4 hours. During the reaction water and toluene were periodically removed from the Dean Stark trap. The final silicone polyamide was poured off at approximately 150 degrees C. while still in the melt form.

Example 4

A 2000 ml three neck flask equipped with a thermometer, electrical stirrer and a condenser was charged with 1536.0 g of dimethylcyclosiloxanes, 64.0 g of tetramethyldihydrogen disiloxane and 1.3 g of trifluoromethane sulfonic acid. The flask was heated to 80 degrees C. and kept at temperature for 4 hours. After 4 hours, 25 g of sodium bicarbonate were added and mixed at 80 degrees C. for another 2 hours. The reaction product was filtered using a 0.8 micron filter paper (45 DP dimethylhydrogen endblocked polydimethyl siloxane). A 3000 ml flask equipped with a thermometer, electrical stirrer,, and a condenser was charged with 2000.0 g of dimethylcyclosiloxanes, 129.9 g of tetramethyldihydrogen disiloxane and 1.67 g of trifluoromethane sulfonic acid. The flask was heated to 80 degrees C. while mixing and kept at temperature for 4 hours. After 4 hours, 45 g of calcium carbonate were added and mixed at 80 degrees for another 2 hours. The reaction product was filtered using a 0.8 micron filter paper (30 DP dimethylhydrogen endblocked polydimethyl siloxane). To a 2000 ml flask equipped with a thermometer, electrical stirrer, condenser, and nitrogen purge were added 250 g of the product (45 DP dimethylhydrogen endblocked polydimethyl siloxane), 1250 g of product II (30 DP dimethylhydrogen endblocked polydimethyl siloxane) and sufficient of the platinum catalyst as described in Example 1. The mixture was heated to 80 degrees C. while mixing. In an addition funnel was placed 334 g of trimethylsilyl protected undecylenic acid; the material was added dropwise to the reactor and an exotherm was observed. After the addition was completed the temperature was increased to 110 degrees C. and the contents were allowed to react for an additional hour. The temperature was then taken to 150 degrees C. under vacuum for approximately 1 hour. The vacuum was removed and the reactor was cooled to below 60 degrees C. Once below 60 degrees C., 85.0 g of methanol were added to the reactor and the temperature was set to 60 degrees C. After 2 hours the temperature was increased to 150 degrees C. under vacuum to remove residual methanol and trimethylmethoxysilane. To a 2000 ml flask equipped with a thermometer, electrical stirrer, condenser, nitrogen purge and a Dean Stark trap were added 1485.1 g of the product (45 DP and 30 DP carboxylic acid endblocked siloxane), 100 g of toluene and 63.0 g of hexamethylenediamine. The reactor temperature was increased to 150 degrees C. for 4 hours. During the reaction, water and toluene were periodically removed from the Dean Stark trap. The final silicone polyamide was poured off at a temperature of approximately 150 degrees while still in the melt form.

Example 5

A 3000 ml three neck flask equipped with a thermometer, electrical stirrer and a condenser was charged with 2000.0 g of dimethylcyclosiloxanes, 129.9 g of tetramethyldihydrogen disiloxane and 1.6 g of trifluoromethane sulfonic acid. The flask was heated to 80 degrees C. and kept at temperature for 4 hours. After 4 hours, 45 g of calcium carbonate wee added and mixed at 80 degrees C. for another 2 hours. The reaction product was filtered using a 0.8 micron filter paper. To a 2000 ml flask equipped with a thermometer, electrical stirrer, condenser and nitrogen purge were added 816 g of the product (30 DP dimethylhydrogen endblocked polydimethyl siloxane) and sufficient of the platinum catalyst as described in Example 1. The mixture was heated to 80 degrees C. while mixing. In an addition funnel was placed 189.0 g of trimethylsilyl protected undecylenic acid; the material was added dropwise to the reactor and an exotherm was observed. After the addition was completed, the temperature was then taken to 150 degrees C. under a vacuum for approximately 1 hour. The vacuum was then removed and the reactor was allowed to cool to a temperature below 60 degrees C. Once below 60 degrees C., 57.1 g of methanol were added to the reactor and the temperature was set at 60 degrees C. After 2 hours, the temperature was increased to 150 degrees under vacuum to remove residual methanol and trimethylmethoxysilane. To a 500 ml flask equipped with a thermometer, electrical stirrer, condenser, nitrogen purge and a Dean Stark trap were added 150 g of the product (30 DP carboxylic acid endblocked siloxane), 39.1 g of toluene, 5.71 g of hexamethylenediamine and 0.72 g of tris(2-aminoethyl)amine. The reactor temperature was increased to 150 degrees C. for 4 hours. During the reaction, water and toluene were periodically removed from the Dean Stark trap. The final silicone polyamide was poured off at a temperature of approximately 150 degrees C. while still in the melt form.

FORMULATION EXAMPLES

The following formulation examples are illustrative of the invention. As referred to in the Formulation Examples, the siloxane-based polyamide of Example 2 is a material as described above in the synthesis of such material.

Example A: Deodorant Stick

The following materials are combined. The amounts given are in percents by weight based on the total weight of the composition.

| | |
|---|---:|
| siloxane-based polyamide from Example 2 (gellant) | 20% |
| cyclomethicone (silicone fluid) | 79% |
| fragrance (deodorant active) | 1% |
| Total | 100% |

Example B

The following is a generic formula for a clear antiperspirant stick.

| Component | Range w/w % | Preferred w/w % |
|---|---|---|
| Oil Phase | | |
| Siloxane-based polyamide gellant | 6–20 | 10–15 |
| Silicone fluids | 10–90 | 20–50 |
| Cosmetic additives | 0–40 | 5–21 |

| Component | Range w/w % | Preferred w/w % |
|---|---|---|
| and/or solvents | | |
| Fragrance, color | QS | QS |
| Polar Phase | | |
| Water and/or water miscible solvent | 10–40 | 15–25 |
| Antiperspirant active | 5–30 | 15–25 |
| Surfactant | 0–10 | 0.5–3 |
| Total | 100 | 100 |

Generalized manufacturing procedure:

1) Weigh all the oil phase components except the fragrance into a kettle and mix and heat until clear, cool to 70–80° C.

2) Weigh all the polar phase components except the surfactant into a separate kettle and mix and heat until clear. When clear, add the surfactant to the salt solution. Continue heating the polar phase to 70–80° C.

3) Add the hot polar phase to the hot oil phase with moderate agitation to avoid air incorporation.

4) Continue mixing and cool to 55–65° C. and add fragrance.

5) Continue cooling to 5–10 degrees C. above the gelation point and pour into containers.

Example C

The following clear antiperspirant stick of with good aesthetics was prepared following the generalized manufacturing procedure described in Example B.

| Component | w/w % |
|---|---|
| Oil Phase | |
| Siloxane-based polyamide of Example 2 | 12.00 |
| Trimethylated silica (Dow Corning ® 749) | 2.50 |
| Behenoxy dimethicone (Abil ® Wax 2440) | 2.50 |
| Cyclomethicone (Dow Corning ® 245) | 29.37 |
| Phenyl trimethicone (Dow Corning ® 556) | 10.00 |
| Isostearyl alcohol (Prisorine ® 3515) | 0.50 |
| Polar Phase | |
| Deionized water | 22.13 |
| Al Zr tetrachlorohydrex gly (Rezal ® 36 GP) | 20.00 |
| Polysorbate 20 | 1.00 |

Examples D–E

Examples D and E were made by the method described in Example B using the components described below. The compositions of Examples D and E were tested by an independent trained panel and were found to have significantly better aesthetics (tack and wetness) than a leading commercial clear antiperspirant stick; better aesthetics (tack) than a leading commercial clear deodorant; and similar aesthetics (tack) to a leading commercial suspension antiperspirant stick.

| Component | Example D % w/w | Example E % w/w |
|---|---|---|
| Oil Phase | | |
| Cyclomethicone (Dow Corning ® 245) | 23.35 | 28.29 |
| Siloxane-based polyamide of Example 2 | 12.00 | 15.00 |
| PPG-3 myristyl ether (Witconol ® APM) | 16.30 | — |
| Behenoxy dimethicone (Abil ® Wax 2440) | 2.00 | 1.50 |
| Isostearyl alcohol (Prisorine ® 3515) | 0.50 | 0.50 |
| Phenyl trimethicone (Dow Corning ® 556) | 5.00 | 10.00 |
| Trimethylated silica (Dow Corning ® 749) | — | 1.50 |
| Polar Phase | | |
| Deionized Water | 18.85 | 21.21 |
| Al Zr tetrachlorohydrex gly (Rezal ® 36 GP) | 20.00 | 20.00 |
| Dimethicone copolyol (Dow Corning ® 193) | 2.00 | 2.00 |

Examples F–G

The following compositions of Examples F and G were made by the method described in Example B using the components described below. These compositions were tested for antiperspiracy and showed parity efficacy to a leading commercial suspension antiperspirant stick

| Component | Example F % w/w | Example G % w/w |
|---|---|---|
| Oil Phase | | |
| Cyclomethicone (Dow Corning ® 245) | 23.60 | 22.42 |
| Siloxane-based polyamide of Example 2 | 12.00 | 12.00 |
| PPG-3 myristyl ether (Witconol ® APM) | 16.30 | 16.30 |
| Behenoxy dimethicone (Abil ® wax 2440) | 2.00 | 2.00 |
| Isostearyl alcohol (Prisorine ® 3515) | 0.50 | 0.50 |
| Phenyl trimethicone (Dow Corning ® 556) | 5.00 | 5.00 |
| Polar Phase | | |
| Deionized Water | 19.60 | 16.78 |
| Al Zr tetrachlorohydrex gly (Rezal ® 36 GP) | 20.00 | 20.00 |
| Dimethicone copolyol (Dow Corning ® 193) | 1.00 | 5.00 |

GEL EXAMPLES

Gel Example 1

The following gel examples were made by the following method using the components described in the table below. All percents are by weight based on the total composition of the composition. A silicone fluid such as cyclomethicone and the gellant (siloxane-based polyamide gellant of the invention) are weighed out and placed into a glass beaker with heating and stirring (250 rotations per minute) until all of the gellant is melted. This typically occurs at about 100 degrees C. The rest of the components of the oil phase is added to the batch after all of the gellant has completely dissolved, and mixing is continued for 10 minutes. The polar phase components are slowly added in aliquots over a 10 minute period while mixing at 300 rotations per minute. Mixing is continued for 15 minutes at 400 rotations per minute while maintaining a temperature of 85 degrees C. The batch is then transferred to a heated homogenizer and homogenized for 2 minutes. Fragrance (if used) is then added and the mixing is continued for another minute. The batch is transferred to the packaging while it is still hot and allowed to set. (Note that while specific stirring rates have been described above, low speed stirring of other values may be substituted for 250 rpm; and moderate speed stirring may be substituted for 300–400 rpm rates.)

In general, suitable ranges for the components are as follows:

| Oil Phase (50–70%) | | |
|---|---|---|
| Siloxane-based polyamide | 0.5–8.0% | preferably 2–6% |
| Silicone Fluid | 20–60% | preferably 35–45% |
| Cosmetic additive(s) and/or solvents | 0–20% | preferably 7–15% |
| Surfactant | 0–10% | preferably 3–7% |
| Fragrance | 0–3% | preferably 1–2% |
| Polar Phase (50–30%) | | |
| Water (and/or water miscible solvent) | 5–40% | preferably 15–25% |
| Antiperspirant Active | 10–25% | preferably 15–25% |
| Surfactant | 0–5% | preferably 1–2% |

Gel Example 2

| INGREDIENT | Percent by Weight % |
|---|---|
| Oil Phase | |
| Cyclomethicone (Dow Corning ® 245) | 41.15 |
| Siloxane-based polyamide of Example 2 | 2.35 |
| Cyclomethicone and dimethicone copolyol (Dow Corning ® 3225C) | 6.00 |
| Isopropyl Myristate | 4.50 |
| PPG-3 Myristyl Ether | 4.50 |
| Fragrance | 1.00 |
| Octylmethoxy cinnamate | 0.50 |
| Total | 60.0000 |
| Polar Phase | |
| Aluminum chlorohydrate (50% aq. solution.) | 40.00 |
| | 40.000 |
| Total | 100.000 |

Gel Example 3

| INGREDIENT | % |
|---|---|
| Oil Phase | |
| Cyclomethicone (Dow Corning ® 245) | 38.00 |
| Siloxane-based polyamide of Example 2 | 6.00 |
| Cyclomethicone and dimethicone copolyol (Dow Corning ® 3225C) | 6.00 |
| Isopropyl Myristate | 4.50 |
| PPG-3 Myristyl Ether | 4.50 |
| Fragrance | 1.00 |

-continued

| INGREDIENT | % |
|---|---|
| Total | 60.0000 |
| Polar Phase | |
| Aluminum chlorohydrate (50% aq. solution.) | 40.00 |
| Total | 40.000 |

Gel Example 4: Clear Gel

The method described above for Gel Example 1 was repeated with the following components where the amounts listed are in percent by weight:

| Oil Phase | |
|---|---|
| Cyclomethicone | 41.15% |
| Siloxane-based polyamide of Example 2 | 2.35% |
| Cyclomethicone/dimethicone copolyol | 6.0% |
| Isopropyl myristate | 4.5% |
| PPG-3 myristyl ether | 4.5% |
| Fragrance | 1.0% |
| Octyl methoxy cinnamate | 0.5% |
| Polar Phase | |
| Aluminum chlorohydrate (50% aqueous solution) | 40.0% |

Suspension Stick Example 1

A siloxane-based polyamide of Example 2 (20 weight percent of the final composition) is dissolved into cyclomethicone (55 weight percent) by heating the mixture to 95 degrees with stirring. When all of the gellant is dissolved, the mixture is cooled to 75 degrees C. The Al/Zr tetrachlorohydrex gly ( 24 weight percent, Reach® 908) is added with stirring. The mixture is cooled to 70 degrees and fragrance (1 weight percent) is added with stirring. The mixture is poured into suitable containers and allowed to cool.

We claim:

1. A base composition made by combining:
   (a) 0.5–80 percent by weight based on the total weight of the composition of at least one siloxane-based polyamide;
   (b) 5–95 percent by weight silicone fluid; and
   (c) if (a)+(b) do not equal 100 percent, then a portion of solvent sufficient to make 100 percent, wherein:
   the siloxane-based polyamide is formed from units of Formula A

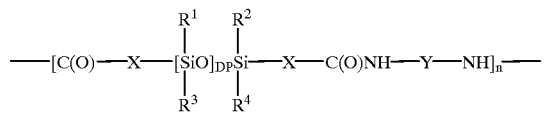

Formula A where:
(1) n is a number selected from the group consisting of 1–500, where n is the number of units in the polyamide;

(2) DP is an average value for degree of polymerization of a siloxane portion of the polyamide and is selected from the group consisting of 1–700;
(3) X is a linear or branched chain alkylene having 1–30 carbons;
(4) each of $R^1$–$R^4$ is independently selected from the group consisting of methyl, ethyl, propyl, isopropyl, a siloxane chain, and phenyl, wherein the phenyl may optionally be substituted by 1–3 members from the group consisting of methyl and ethyl; and
(5) Y is selected from the group consisting of linear or branched chain alkylenes having 1–40 carbons, wherein the alkylene group itself may optionally be substituted by at least one member selected from the group consisting of
  (i) hydroxy;
  (ii) $C_3$–$C_8$ cycloalkane;
  (iii) 1–3 members selected independently from the group consisting of C1–C3 alkyls; phenyl optionally substituted by 1–3 members independently selected from the group consisting of C1–C3 alkyls;
  (iv) C1–C3 alkyl hydroxy; and
  (v) C1–C6 alkyl amine;
or Y may be Z where Z=$R^{20}$ T($R^{22}$)$R^{21}$ where each of $R^{20}$, $R^{21}$ and $R^{22}$ is independently selected from the group consisting of linear and branched C1–C10 alkyl or alkylene groups; and T is selected from the group consisting of CR, where R is selected from the group consisting of hydrogen, the group consisting of the group defined for $R^1$–$R^4$; and a trivalent atom selected from the group consisting of N, P and Al; and wherein each value for X, Y, DP and $R^1$–$R^4$ may be the same or different for each unit in the polyamide to form a clear stick or gel.

2. A cosmetic composition made by combining
(a) a base composition made by combining:
  (i) 0.5–80 percent by weight based on the total weight of the composition of at least one siloxane-based polyamide as described in claim 1;
  (ii) 5–95 percent by weighs silicone fluid; and
(b) at least one additional ingredient selected from the group consisting of cosmetically active additives and cosmetically acceptable solvents wherein the total amount of the additional ingredients added is in the range of 0.1–85% by weight based on the total weight of the cosmetic composition to form a clear stick or gel.

3. A cosmetic composition according to claim 2 which is a gel and wherein the amount of siloxane-based polyamide is in the range of 0.5–8%.

4. A cosmetic composition according to claim 2 which is a stick and wherein the amount of siloxane-based polyamide is in the range of 5–30%.

5. A cosmetic composition made by combining based on the total weight of the composition:
(a) a base composition made by combining:
  (i) 0.5–80 percent by weight of at least one siloxane-based polyamide as described in claim 1;
  (ii) 5–95 percent by weight silicone fluid; and
  (iii) optionally up to 40 percent by weight of at least one solvent; and
(b) 0.1–85 percent by weight of at least one additional ingredients selected from the group consisting of
  (i) 0.1–30 weight percent of an antiperspirant active;
  (ii) 0.5–3.0 weight percent of a fragrance;
  (iii) 0.2–1.0 weight percent of a bacteriostat; and
  (iv) 0–15 weight percent of a surfactant;
  (v) an effective amount of a sunscreen;
  (vi) an effective amount of an insect repellant; and
  (vii) water.

6. A cosmetic composition as claimed in claim 5 wherein the amount of siloxane-based polyamide is in the range of 0.5–8 weight percent.

7. A cosmetic composition as claimed in claim 5 wherein the amount of siloxane-based polyamide is in the range of 6–20 weight percent.

8. A cosmetic composition as claimed in claim 5 wherein the silicone fluid is selected from the group consisting of volatile silicones, non-volatile silicones and mixtures of volatile silicones and non-volatile silicones.

9. A cosmetic composition as claimed in claim 8 wherein the silicone fluid is selected from the group consisting of dimethicones, phenyl trimethicone, and cyclic siloxanes having from 4–6 siloxane units in a ring optionally substituted by C1–C6 alkyl or phenyl.

10. A cosmetic composition as claimed in claim 2 wherein the cosmetic active additive is an antiperspirant selected from the group consisting of aluminum chlorohydrate, aluminum chloride, aluminum sesquichlorohydrate, zirconyl hydroxychloride, aluminum-zirconium glycine complex, aluminum chlorohydrex PG, aluminum chlorohydrex PEG, aluminum dichlorohydrex PG, and aluminum dichlorohydrex PEG, aluminum nitratohydrate and its combination with zirconyl hydroxychlorides and nitrates, and aluminum-stannous chlorohydrates.

11. A cosmetic composition as claimed in claim 5 wherein the bacteriostat is selected from the group consisting of 2-amino-2-methyl-1-propanol (AMP), cetyltrimethylammonium bromide, cetyl pyridinium chloride, 2,4,4'-trichloro-2'-hydroxydiphenylether, N-(4-chlorophenyl)-N'-(3,4-dichlorophenyl)urea and zinc salts.

12. A cosmetic composition as claimed in claim 5 made with the following components where all components are in percent by weight based on the total weight of the composition:

| Oil Phase (50–70%) | |
| --- | --- |
| Siloxane-based polyamide | 0.5–8.0% |
| Silicone fluid | 20–60% |
| Cosmetic additive(s) and/or solvents | 0–20% |
| Surfactant | 0–10% |
| Fragrance | 0–3% |
| Polar Phase (50–30%) | |
| Water (and/or water miscible solvent) | 5–40% |
| Antiperspirant active | 10–25% |
| Surfactant | 0–5% |

13. A cosmetic composition as claimed in claim 12 made with the following components:

| Oil Phase (50–70%) | |
| --- | --- |
| Siloxane-based polyamide | 2–6% |
| Silicone fluid | 35–45% |
| Cosmetic additive(s) and/or solvents | 7–15% |
| Surfactant | 3–7% |
| Fragrance | 1–2% |

-continued

| Polar Phase (50–30%) | |
|---|---|
| Water (and/or water miscible solvent) | 15–25% |
| Antiperspirant active | 15–25% |
| Surfactant | 1–2% |

14. A cosmetic composition as claimed in claim 5 made with the following components wherein the components are in percent by weight based on the total weight of the composition:

| Oil Phase | |
|---|---|
| Siloxane-based polyamide gellant | 6–20% |
| Silicone fluids | 10–90% |
| Cosmetic additives and/or solvents | 0–40% |
| Fragrance, color | QS |
| Polar Phase | |
| Water and/or water miscible solvent | 10–40% |
| Antiperspirant active | 5–30% |
| Surfactant | 0–10% |
| Total | 100 |

15. A composition as claimed in claim 14 made with the following components:

| Oil Phase | |
|---|---|
| Siloxane-based polyamide gellant | 10–15% |
| Silicone fluids | 20–50% |
| Cosmetic additives and/or solvents | 5–21% |
| Fragrance, color | QS |
| Polar Phase | |
| Water and/or water miscible solvent | 15–25% |
| Antiperspirant active | 15–25% |
| Surfactant | 0.5–3% |
| Total | 100 |

16. A cosmetic composition comprising a silicone polyamide having at least one repeating unit represented by the formula

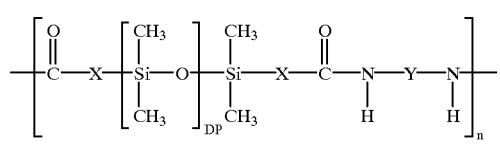

wherein X is a linear or branched $C_1$–$C_{30}$ alkylene chain; Y is a linear or branched $C_1$–$C_{20}$ alkylene chain; DP is an integer having a value of 15–500; n is an integer having a value of 1–500;

with the proviso that Y can also represent

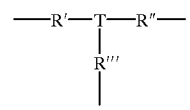

for providing linkage to another repeating unit, in which case R', R", and R'" are linear or branched $C_1$–$C_{10}$ alkyl or alkylene groups; and T is $\equiv$CH, N, P, or Al.

17. A cosmetic composition according to claim 16 in which the silicone polyamide has a number average molecular weight of from 4,000 to 200,000 daltons, as determined by gel permeation chromatography using polydimethylsiloxane as a standard.

18. A cosmetic composition according to claim 17 in which the silicone polyamide has a number average molecular weight of from 5,000 to 50,000 daltons, as determined by gel permeation chromatography using polydimethylsiloxane as a standard.

19. A cosmetic composition according to claim 16 including a silicone fluid selected from the group consisting of cyclomethicones, dimethicones, and phenyltrimethicones.

20. A cosmetic composition according to claim 16 in which the repeating unit of the silicone polyamide is represented by the formula

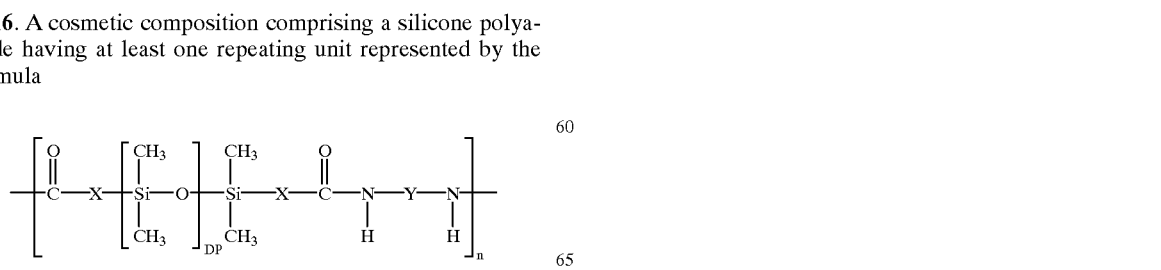

or the formula

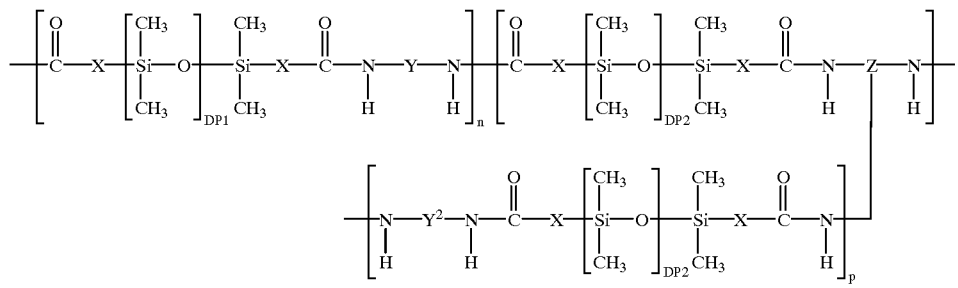

wherein X is a linear or branched $C_1$–$C_{30}$ alkylene chain; Y, $Y^1$, and $Y^2$ are linear or branched $C_1$–$C_{20}$ alkylene chain; DP1, DP2, and DP3 are integers each having values of 15–500; n, m, and p are integers each having values of 1–500; Z is represented by

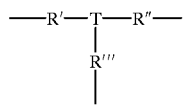

wherein R', R", and R'" are linear or branched $C_1$–$C_{10}$ alkyl or alkylene groups; and T is ≡CH, N, P, or Al; provided n is not the same as m, or Y is not the same as $Y^1$, or DP1 is not the same as DP2.

* * * * *